United States Patent [19]

Chaudhari et al.

[11] Patent Number: 5,502,241
[45] Date of Patent: Mar. 26, 1996

[54] PROCESS FOR THE PREPARATION OF ALKYL CARBAMATES

[75] Inventors: Raghunath V. Chaudhari; Sunil P. Gupte; Ashutosh A. Kelkar, all of Maharashtra; Devidas S. Kolhe, deceased, late of Pune, all of Ind., by Poornima D. Kolhe, heir

[73] Assignee: Council of Scientific & Industrial Research, New Delhi, Ind.

[21] Appl. No.: 307,393

[22] Filed: Sep. 16, 1994

Related U.S. Application Data

[63] Continuation of Ser. No. 812,753, Dec. 23, 1991, abandoned, which is a continuation-in-part of Ser. No. 475,747, Feb. 6, 1990, abandoned.

[51] Int. Cl.$^6$ .................................................... C07C 269/04
[52] U.S. Cl. ............................................ 560/157; 560/24
[58] Field of Search ............................... 560/157, 24

[56] References Cited

U.S. PATENT DOCUMENTS

| | | | |
|---|---|---|---|
| 4,297,501 | 10/1981 | Becker et al. | 560/157 |
| 4,582,923 | 4/1986 | Slammann et al. | 560/157 |
| 4,621,149 | 11/1986 | Fukuoka et al. | 560/157 |
| 4,694,097 | 9/1987 | Alper et al. | 560/157 |

FOREIGN PATENT DOCUMENTS

| | | | |
|---|---|---|---|
| 58-146548 | 9/1983 | Japan | 560/157 |
| 58-146549 | 9/1983 | Japan | 560/157 |
| 58-148844 | 9/1983 | Japan | 560/157 |
| 58-150555 | 9/1983 | Japan | 560/157 |

*Primary Examiner*—James H. Reamer
*Attorney, Agent, or Firm*—Ladas & Parry

[57] ABSTRACT

The invention relates to an efficient process for the preparation of methyl methyl carbamate by reacting methyl amine or N,N'-dimethyl urea with carbon monoxide, an oxidizing agent and a monoalcohol in the presence of a catalyst system including (i) a precursor selected from the group consisting of platinum group metals and soluble compounds of platinum group metals, and (ii) a promoter comprising at least one halogen containing compound selected from the group consisting of alkali metal halides, alkaline earth metal halides, quaternary ammonium halides, oxo acids of halogen atoms and their salts, and complex compounds containing halogen ions, organic halides and halogen molecules.

12 Claims, No Drawings

PROCESS FOR THE PREPARATION OF ALKYL CARBAMATES

This is a continuation of application Ser. No. 07/812,753 filed on Dec. 23, 1991, now abandoned which is a continuation-in-part of application Ser. No.: 07/475,747 filed Feb. 6, 1990 (now abandoned).

The present invention relates to an improved process for the preparation of alkyl carbamates by the oxidative carbonylation of NH-containing hydrocarbon compounds, specifically amines and alkyl ureas. Examples of the carbamates which can be prepared by the inventive process include methyl methyl carbamate, methyl ethyl carbamate and methyl butyl carbamate.

Alkyl carbamates have in the past been manufactured by phosgination of aliphatic amines. According to this prior art process, aromatic or aliphatic amines are reacted with phosgene to produce isocyanates which are then reacted with alcohol to produce the desired carbamates.

Unfortunately, the phosgination process employs starting materials such as phosgene and isocyanates which are toxic and therefore hazardous and this renders this particular process unsafe. Furthermore, the step of phosgination results in the generation of hydrochloric acid which is the cause of severe problems of corrosion and it will be appreciated that corrosion of production systems is particularly undesirable in such a process.

Accordingly, there has been a long-felt need to develop a process for the preparation of alkyl carbamates, particularly methyl methyl carbamate, which avoids the use of the toxic starting materials of phosgene and isocyanates. To this end there have been a number of efforts. For instance, a process for the oxidative carbonylation of aromatic amines to aryl carbamates has been reported in JP 58,146,549, 1983 and a number of catalysts for such a process selected from the elements referred to in Group VIa of the Periodic Table have been proposed (Journal of the American Chemical Society 93, 6344, 1971; Bull Chem. SAoc. Japan 57, 251, 1984 and Agew. Chem. Int. Ed. [England] 18, 692, 1979). Regrettably, such process suffer from the disadvantage that the oxidative carbonylation reactions are all stoichiometric in nature and not truly catalytic.

Another process which has been proposed for the oxidative carbonylation of amines involves the use of palladium chloride and a Lewis acid which must contain metal components capable of undergoing redox reactions such as $CuCl_2$, $FeCl_3$ and $FeOCl$. This process has been described in German Patents Nos. 2908250 and 2910132, U.S. Pat. Nos. 4,304,922 and 4,297,560 and European Patent No. 36895. However, this further process possesses the drawback that solutions of the chlorides mentioned are highly corrosive and regeneration of the catalyst is often difficult.

More recently, there has been proposed a process for the oxidative carbonylation of aromatic amines to produce aryl carbamates in which supported noble metal catalysts are employed. Examples of the noble metals constituting such catalysts include rhodium, iridium, palladium, platinum and ruthenium. Conventionally, alkali metal halides are used as promoters in conjunction with such catalysts. Processes of this nature have been described in Japanese Patents Nos. 58 146,549, 58 144,363 and 58 150,555, all of 1983, Journal Chem. Soc. Chem. Commun., 339, 1984, Journal Org. Chem. 49, 1984 and Chemtech, 6 70, 1984.

This recent process achieves a very high yield of carbamates with almost 100% selectivity. However, the processes described all relate exclusively to the synthesis of aryl carbamates and there are, to the applicants' knowledge, no processes known for the preparation of alkyl carbamates by the oxidative carbonylation of NH-containing hydrocarbons such as alkyl amines or dialkyl urea derivatives, and specifically for the preparation of methyl methyl carbamate. From the literature (Ref. Chem. Comm. page 380, 1966; J. Chem. Comm. page 307, 1972; J. Amer. Chem. Soc. 93, page 6344, (1971)) it is seen that the reactivity of the alkyl and aryl amines is drastically different in the synthesis of urea by oxidative carbonylation of amines. Therefore, the synthesis and efficiency of synthesis of alkyl carbamates cannot be predicted from the synthesis of aryl carbamates. Nevertheless, with the potential application of alkyl carbamates such as methyl methyl carbamate in the synthesis of insecticides, such as methyl-naphthyl carbamate (Carbaryl), 2-sec butyl methyl carbamate (BPMC) and carbofuran, there is an urgent need for the development of an efficient process for the synthesis of alkyl carbamate derivatives and specifically methyl methyl carbamate.

It is therefore the basic object of the present invention to provide an improved process for the preparation of alkyl carbamates which avoids the drawbacks referred to above.

A more specific object of the invention resides in the provision of an improved process for the preparation of alkyl carbamates which avoids the employment of hazardous or toxic compounds such as phosgene and/or methyl isocyanate as starting materials and which can be effected under mild conditions of temperature and pressure.

A further object of the invention resides in the provision of an improved process for the preparation of alkyl carbamates by the oxidative carbonylation of NH-containing hydrocarbons.

Accordingly, the present invention provides a process for the preparation of alkyl carbamates which comprises reacting at least one compound selected from the group consisting of primary alkyl amines, secondary alkyl amines and dialkyl ureas with carbon monoxide, an oxidizing agent and an organic hydroxyl compound selected from aliphatic monoalcohols having from 1 to 10 carbon atoms and alicyclic monoalcohols having from 3 to 10 carbon atoms, said reaction being conducted in the presence of a catalyst system consisting of (i) a precursor selected from the platinum group of metals or compounds containing at least one platinum group element and (ii) a promotor comprising at least one halogen-containing compound.

The overall reactions envisaged by the process of the present invention are as follows:

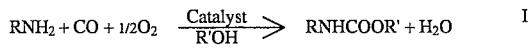
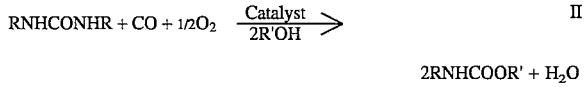

wherein R is alkyl and R' is an aliphatic monoalcohol having from 1 to 10 carbon atoms or an alicyclic monoalcohol having from 3 to 10 carbon atoms.

Examples of the primary aliphatic amine that can be employed in the process of the present invention include methyl amine, ethyl amine, propyl amine, butyl amine, diamines such as ethylene diamine, diaminopropane, diaminobutene and the like.

The secondary aliphatic amines which can be employed in the inventive process include dimethyl amine, diethyl amine, dipropyl amine and the like.

The urea compounds also capable of being employed as starting materials in the process of the present invention include N,N'-dimethyl urea, N,N'-diethyl urea, N,N'-dipropyl urea and the like.

The carbon monoxide employed in the process of the present invention may be pure gaseous carbon monoxide but may also contain impurities such as nitrogen and carbon dioxide. An impurity content of less than 10% volume per volume does not affect the reaction pattern and from the industrial viewpoint, it may be advantageous to use carbon monoxide with small amounts of impurities. Carbon monoxide is employed in an amount of at least one mole per amino group of the primary or secondary alkyl amine or per urea group of the urea compound. A more preferred amount of carbon monoxide is from 2 to 100 moles per amino group of the primary or secondary alkyl amine or per urea group of the urea compound.

The oxidizing agent used in the process of the invention may be pure oxygen or a gas containing oxygen such as air. The process also tolerates the employment in some cases of and oxygen-containing gas which additionally contains other non-interfering gases such as nitrogen, argon or carbon dioxide.

The organic hydroxyl compound which forms one of the reactants can also function as a solvent. However, where necessary, other solvents which do not affect the reaction adversely may also be used. Exemplary of such solvents are aromatic hydrocarbons such as benzene, toluene, xylene and mesitylene, nitriles such as acetonitrile and benzonitrile, ethers such as tetrahydrofuran and 2-dioxane, ketones such as acetone and methyl ethyl ketone, amides such as N,N'-dimethyl formamide and N,N'-dimethyl acetamide, and esters such as ethyl acetate and ethyl benzoate.

Component (i) of the catalyst system which acts as a precursor can comprise one or more transition metals or one or more soluble compounds of such metals supported, if desired, on a suitable carrier. Of the transition metals, rhodium and palladium are preferred with palladium being specially preferred.

Specific examples of the catalyst precursors include Pd black, supported palladium catalysts such as Pd-C, Pd-Al$_2$O, PD-CaCO$_3$ and the like, and intermetallic compounds such as Pd-Se, Pd-Co, Pd-Rh and the like. Pd black which has been prepared by various reducing agents such hydrazine hydrate, sodium formate, formaldehyde, sodium borohydride, LiAlH$_4$ and H$_2$ can also be used.

Soluble Pd compounds that can be used are PdCl$_2$, PdBr$_2$, PdI$_2$, Pd(NO$_3$)$_2$, Pd(OCOCH$_3$)$_2$, Pd-oxalate, [Pd(NH$_3$)$_4$] X$_2$, [PdL$_2$X ], [Pd(CO)X] wherein X is chlorine, bromine or iodine and L is triphenyl phosphine, pyridine, isoquinoline, tributyl phosphine, benzonitrile and the like.

Metallic rhodium, intermetallic compounds of rhodium and supported rhodium compounds similar to catalyst precursors prepared of or from palladium as described above can also be used. Soluble rhodium complexes that can be used include RhCl$_3$, RhI$_3$, [Rh(CO)$_2$Cl]$_2$, RhCl(PPh$_3$)$_3$, RhX (CO)L$_2$ wherein X is chlorine, bromine or iodine and L is triphenyl phosphine, tributyl phosphine, triphenyl arsine and the like.

The halogen containing promotor which constitutes component (ii) of the catalyst system can be selected from alkali metal halides, alkaline earth metal halides, quaternary ammonium halides, oxo acids of halogen atoms and their salts, and complex compounds containing halogen ions, organic halides and halogen molecules. However, of all the halogens compounds, which act as promoters, those compounds containing iodine are particularly preferred. These include sodium iodide, potassium iodide, lithium iodide, cesium iodide, tetrabutyl ammonium iodide, tetraheptyl ammonium iodide, iodous acid, iodic acid, iodine and the like.

The oxidative carbonylation reaction of the present invention can be carried out in a temperature range of 80° C. to 350° C., more preferably between 120° C. and 250° C.

However, it has been found that temperature is an important factor in obtaining a good yield of carbamate derivatives. Thus, at lower temperatures (<140° C.), selectivity to MMC is very poor.

Preferably, the carbonylation is carried out under a carbon monoxide partial pressure of about 5 to 6000 psig, more preferably between 100 and 1500 psig. The partial pressure of oxygen employed is between 5 and 1000 psig, more preferably between 10 and 300 psig. The ratio of CO/O$_2$ used in this process is an important factor and activity and selectivity of the catalyst was found to be drastically affected when the CO/O$_2$ ratio was varied. The ratio of CO:O$_2$ in the reactor can be in the range of from 1:1 to 50:1, preferably in the range of from 5:1 to 20:1.

In giving effect to the reaction of the present invention, it has been found convenient to employ 1 mol of catalyst per 5 to 8000 mols of primary or secondary alkyl amine or urea compound. A more preferred range comprises one mol of catalyst per 100 to 500 mols of alkyl amine or urea compound.

The amount of primary or secondary alkyl amine or urea compound used is found to be a very important factor in determining the selectivity of carbamate. It may be noted that prior art does not mention the influence of the amount of amine used on the selectivity of the carbamate derivative (Fukuoka et al. U.S. Pat. No. 4,621,149 dated Nov. 4, 1986 [column 12 line 58 to column 16 line 56]).

It has been found that, if the concentration of methyl amine or N,N'dimethyl urea is properly selected, the process of present invention may be used to result in a 90% to 95% conversion of methyl amine or N,N'dimethyl urea with a 85% to 90% yield of methyl methyl carbamate and a selectivity of 80% to 90%.

To achieve the maximum selectivity and yield of methyl methyl carbamate, the concentration of methyl amine compound in the reactor should be in the range of $1 \times 10^{-5}$ to $1.18 \times 10^{-2}$ mol/cm$^3$, preferably from $1 \times 10^{-4}$ to $2.5 \times 10^{-3}$ mol/cm$^3$ and most preferably from $3.2 \times 10^{-4}$ to $1.6 \times 10^{-3}$ mol/cm$^3$. While, the concentration of N,N'dimethyl urea compound in the reactor should be in the range of $1 \times 10^{-5}$ to $0.8 \times 10^{-2}$ mol/cm$^3$, preferably from $1 \times 10^{-4}$ to $2.5 \times 10^{-3}$ mol/cm$^3$ and most preferably from $3.2 \times 10^{-4}$ to $1.0 \times 10^{-3}$ mol/cm$^3$. A concentration of amine or urea compound within these ranges is critical because, as per following reaction.

III    $CH_3NHCONHCH_3 + CH_3OH \rightleftharpoons CH_3NHCOOCH_3 + CH_3NH_2$ methyl methyl carbamate is formed by a non-catalytic reaction between N,N'dimethyl urea and methanol. This reaction is an equilibrium reaction. Therefore, as the concentration of methyl methyl carbamate increases, the formation of N,N'dimethyl urea also increases by the reverse reaction, resulting in lower yields as well as selectivity to methyl methyl carbamate. Our observation indicates that, at higher methyl amine or N,N'dimethyl urea concentration in the reactor (above $2.0 \times 10^{-3}$ mol/cm$^3$, see examples 32, 33, 35 & 36) the yield of methyl methyl carbamate is less than about 40%.

As shown by examples 15 to 36 which follow, the initial concentration of methyl amine or N,N'dimethyl urea is critical to the efficient formation of methyl methyl carbamate according to the present invention. The higher concentration of methyl amine or N, N'dimethyl urea will result in substantially lower yields of methyl methyl carbamate, under given set of reaction conditions. The scientific basis for the lower yields is as discussed above.

Within the catalyst, the ratio of halogen promoter to precursor is preferably in the range of from 0.1 to 10, more preferably between 0.5 and 5.

The amount of organic hydroxyl compound employed is at least one mol per amine group of the primary or secondary alkyl amine or per urea group of the dialkyl urea compound. However, it is more preferable to use 3 to 100 mols of the hydroxyl compound per amino group of the primary or secondary amine or per urea group of the dialkyl urea compound.

The carbamates produced by the process of the present invention find employment in the manufacture of isocyanates, urethane foams, coatings and fibres, pesticides and insecticides. They are particularly applicable for the production of carbamate insecticides such as carbaryl, the generic name for (1-naphthyl-N-methyl carbamate which is sold under the trade name "SEVIN", 2-sec butyl phenyl methyl carbamate popularly known as BPMC and carbofuran. The present invention is of particular significance as it will provide a safer process in which the use of toxic compounds such as phosgene and methyl isocyanate (MIC) will be completely eliminated.

The invention will now be described in detail in the following examples which should not however be construed to limit the scope of the inventive process.

EXAMPLE 1

Methyl methyl carbamate was prepared by charging the following components to a 300 ml stirred autoclave:
Methyl amine: 48.38 mmol
$PdPy_2Cl_2$: 4.73 mmol
Sodium iodide: 4.72 mmol
Methanol: 2412.60 mmol The contents were heated to 150° C. Then autoclave was pressurized with 100 psig of oxygen and then further pressurized up to 1000 psig with carbon monoxide. The pressure in the reactor was maintained constant at 1000 psig, and the progress of the reaction was monitored by observing the pressure drop in the $CO/O_2$ reservoir. The reaction was continued for 6.5 hours. The reactor was then cooled and the liquid phase was analyzed by gas chromatography. GC analysis showed 96.7% conversion of methylamine and the yield of methyl methyl carbamate was 45.96 mmol.

EXAMPLE 2

Methyl methyl carbamate was produced by charging the following components to a 300 ml stirred autoclave:
Methyl amine: 64.52 mmol
Pd $(PPh_3)_2Cl_2$: 4.72 mmol
Lithium iodide: 4.73 mmol
Methanol: 2394.6 mmol The reaction was carried out in accordance with the procedure described in Example 1 and the liquid phase was analyzed by gas chromatography (GC) at the end of the reaction. After 6 hours, GC analysis showed 94.8% conversion of methylamine and the yield of methyl methyl carbamate was 60.23 mmol.

EXAMPLE 3

Methyl methyl carbamate was produced by charging the following components to a 300 ml stirred autoclave:
Methyl amine: 64.52 mmol
Pd $(PhNC)_2Cl_2$: 4.72 mmol
Lithium iodide: 4.72 mmol
Methanol: 2394.6 mmol The reaction was carried out in accordance with the procedure described in Example 1 and the liquid phase was analyzed by gas chromatography (GC) at the end of the reaction. After 6.5 hours, GC analysis showed 95.0% conversion of methylamine and the yield of methyl methyl carbamate was 60.12 mmol.

EXAMPLE 4

Methyl methyl carbamate was produced by charging the following components to a 300 ml stirred autoclave:
Methyl amine: 80.6 mmol
Palladium metal: 4.72 mmol
Lithium iodide: 4.73 mmol
Methanol: 2375.6 mmol The reaction was carried out in accordance with the procedure described in Example 1 and the liquid phase was analyzed by gas chromatography (GC) at the end of the reaction. After 5.5 hours, GC analysis showed 94.5% conversion of methylamine and the yield of methyl methyl carbamate was 70.92 mmol.

EXAMPLE 5

Methyl methyl carbamate was produced by charging the following components to a 300 ml stirred autoclave:
Methyl amine: 80.6 mmol
Palladium chloride: 4.72 mmol
Lithium iodide: 4.73 mmol
Methanol: 2375.6 mmol The reaction was carried out in accordance with the procedure described in Example 1 and the liquid phase was analyzed by gas chromatography (GC) at the end of the reaction. After 5.5 hours, GC analysis showed 94.1% conversion of methylamine and the yield of methyl methyl carbamate was 70.92 mmol.

EXAMPLE 6

Methyl methyl carbamate was produced by charging the following components to a 300 ml stirred autoclave:
Methyl amine: 80.6 mmol
Palladium metal: 4.72 mmol
Potassium iodide: 4.71 mmol
Methanol: 2375.6 mmol The reaction was carried out in accordance with the procedure described in Example 1 except that potassium iodide replaced lithium iodide and the liquid phase was analyzed by gas chromatography (GC) at the end of the reaction. After 6.2 hours, GC analysis showed 91.0% conversion of methylamine and the yield of methyl methyl carbamate was 70.9 mmol.

EXAMPLE 7

Methyl methyl carbamate was produced by charging the following components to a 300 ml stirred autoclave:
Methyl amine: 80.6 mmol
Palladium metal: 4.72 mmol
Tetrabutyl ammonium iodide: 4.73 mmol
Methanol: 2375.6 mmol The reaction was carried out in accordance with the procedure described in Example 1 except that tetrabutyl ammonium iodide replaced lithium iodide and the liquid phase was analyzed by gas chromatography (GC) at the end of the reaction. After 6.5 hours, GC analysis showed 91.3% conversion of methylamine and the yield of methyl methyl carbamate was 72.4 mmol.

EXAMPLE 8

Methyl methyl carbamate was produced by charging the following components to a 300 ml stirred autoclave:
Methyl amine: 80.6 mmol
Palladium metal: 4.72 mmol
Sodium iodide: 4.73 mmol
Methanol: 2375.6 mmol The reaction was carried out in accordance with the procedure described in Example 1 except that sodium iodide replaced lithium iodide and the liquid phase was analyzed by gas chromatography (GC) at the end of the reaction. After 6.5 hours, GC analysis showed 93.1% conversion of methylamine and the yield of methyl methyl carbamate was 74.0 mmol.

EXAMPLE 9

Methyl methyl carbamate was produced by charging the following components to a 300 ml stirred autoclave:
Methyl amine: 80.6 mmol
Palladium metal: 4.72 mmol
Lithium iodide: 4.73 mmol
Methanol: 2375.6 mmol The reaction was carried out in accordance with the procedure described in Example 1 except that the reaction temperature was 170° C. instead of 150° C. The liquid phase was analyzed by gas chromatography (GC) at the end of the reaction. After 5.5 hours, GC analysis showed 98.0% conversion of methylamine and the yield of methyl methyl carbamate was 72.2 mmol.

EXAMPLE 10

Methyl methyl carbamate was produced by charging the following components to a 300 ml stirred autoclave:
Methyl amine: 32.25 mmol
Palladium metal: 4.72 mmol
Lithium iodide: 4.73 mmol
Methanol: 2431.2 mmol The reaction was carried out in accordance with the procedure described in Example 1 and the liquid phase was analyzed by gas chromatography (GC) at the end of the reaction. After 5.6 hours, GC analysis showed 98.5% conversion of methylamine and the yield of methyl methyl carbamate was 28.38 mmol.

EXAMPLE 11

Methyl methyl carbamate was produced by charging the following components to a 300 ml stirred autoclave:
N,N'-dimethyl urea: 56.7 mmol
Palladium metal: 4.72 mmol
Sodium iodide: 4.73 mmol
Methanol: 2362.1 mmol The reaction was carried out in accordance with the procedure described in Example 1 except that N,N'-dimethyl urea replaced methyl amine and the liquid phase was analyzed by gas chromatography (GC) at the end of the reaction. After 6.3 hours, GC analysis showed 100% conversion of N,N'-dimethyl urea and the yield of methyl methyl carbamate was 95.5 mmol.

EXAMPLE 12

Methyl ethyl carbamate was produced by charging the following components to a 300 ml stirred autoclave:
Ethyl amine: 55.4 mmol
Palladium metal: 4.71 mmol
Sodium iodide: 4.73 mmol
Methanol: 2379.62 mmol The reaction was carried out in accordance with the procedure described in Example 1 except that ethyl amine replaced methyl amine and the liquid phase was analyzed by gas chromatography (GC) at the end of the reaction. After 6.5 hours, GC analysis showed 88% conversion of ethyl amine and the yield of methyl ethyl carbamate was 48.19 mmol.

EXAMPLE 13

Methyl butyl carbamate was produced by charging the following components to a 300 ml stirred autoclave:
Butyl amine: 34.18 mmol
Palladium metal: 4.71 mmol
Sodium iodide: 4.73 mmol
Methanol: 2386.74 mmol The reaction was carried out in accordance with the procedure described in Example 1 except that butyl amine replaced methyl amine and the liquid phase was analyzed by gas chromatography (GC) at the end of the reaction. After 7.0 hours, GC analysis showed 91% conversion of butyl amine and the yield of methyl butyl carbamate was 30.76 mmol.

EXAMPLE 14

Methyl methyl carbamate was produced by charging the following components to a 300 ml stirred autoclave:
Methyl amine: 80.6 mmol
$RhCl_3 \cdot 3H_2O$: 4.72 mmol
Sodium iodide: 4.73 mmol
Methanol: 2283.5 mmol The reaction was carried out in accordance with the procedure described in Example 1 and the liquid phase was analyzed by gas chromatography (GC) at the end of the reaction. After 5.2 hours, GC analysis showed 95.2% conversion of methyl amine and the yield of methyl methyl carbamate was 68.51 mmol.

EXAMPLES 15 TO 30

Methyl methyl carbamate was produced by carrying out the reaction in accordance with the procedure described in Example 1, except that the process parameters were varied as shown in Table I. The liquid phase was analyzed by gas chromatography (GC) at the end of the reaction. The results are presented in Table 1.

TABLE I

| EXAMPLE NO. | CATALYST LOADING Pd (mmol.) | Promotor NaI (mmol.) | METHYL AMINE, (mmol.) | $CO/O_2$ RATIO | TEMP. °C. | CONVERSION OF METHYL AMINE (%) | YIELD OF MMC (mmol.) |
|---|---|---|---|---|---|---|---|
| 15. | 4.70 | 4.60 | 96.7 | 13:1 | 170 | 99.56 | 84.03 |
| 16. | 0.47 | 0.46 | 96.7 | 13:1 | 170 | 98.95 | 82.92 |
| 17. | 0.235 | 0.230 | 96.7 | 13:1 | 170 | 98.91 | 82.84 |
| 18. | 0.094 | 0.092 | 96.7 | 13:1 | 170 | 75.34 | *52.77 |
| 19. | 0.235 | 0.230 | 635.5 | 13:1 | 170 | 99.25 | *65.77 |
| 20. | 0.235 | 0.230 | 323.0 | 13:1 | 170 | 98.75 | *100.64 |
| 21. | 0.235 | 0.230 | 161.0 | 13:1 | 170 | 98.42 | 137.22 |
| 22. | 0.235 | 0.230 | 96.7 | 10:1 | 170 | 98.17 | 82.98 |
| 23. | 0.235 | 0.230 | 96.7 | 20:1 | 170 | 99.20 | *23.52 |
| 24. | 0.235 | 0.230 | 96.7 | 25:1 | 170 | 98.64 | *8.15 |
| 25. | 0.235 | 0.230 | 96.7 | 13:1 | 80 | 99.51 | *0.19 |
| 26. | 0.235 | 0.230 | 96.7 | 13:1 | 140 | 98.48 | *51.20 |
| 27. | 0.235 | 0.230 | 96.7 | 13:1 | 150 | 99.23 | 79.77 |
| 28. | 0.235 | 0.230 | 96.7 | 13:1 | 160 | 98.83 | 81.07 |
| 29. | 0.235 | 0.230 | 96.7 | 13:1 | 180 | 98.82 | 83.31 |
| 30. | 0.235 | 0.230 | 96.7 | 13:1 | 190 | 99.38 | 83.12 |

*Lower yields are due to formation of dimethyl urea and N-methyl formamide.

EXAMPLE—31

Methyl methyl carbamate was produced by charging following components to a 300 ml stirred autoclave:
Methyl amine: 150.00 mmol
Palladium metal: 4.72 mmol
Sodium iodide: 4.73 mmol
Methanol: 2292.14 mmol The reaction was carried out as per the procedure described in example 1, and liquid phase was analyzed by gas chromatography. After 6 hrs GC analysis showed 91.0% conversion of methyl amine and yield of methyl methyl carbamate was 121.48 mmol.

EXAMPLE—32

Methyl methyl carbamate was produced by charging following components to a 300 ml stirred autoclave:
Methyl amine: 322.58 mmol
Palladium metal: 4.72 mmol
Sodium iodide: 4.73 mmol
Methanol: 2088.94 mmol The reaction was carried out as per the procedure described in example 1, and liquid phase was analyzed by gas chromatography. After 7.5 hrs GC analysis showed 90.0% conversion of methyl amine and yield of methyl methyl carbamate was 72.58 mmol.

EXAMPLE—33

Methyl methyl carbamate was produced by charging following components to a 300 ml stirred autoclave:
Methyl amine: 645.16 mmol
Palladium metal: 4.72 mmol
Sodium iodide: 4.73 mmol
Methanol: 1709.13 mmol The reaction was carried out as per the procedure described in example 1, and liquid phase was analyzed by gas chromatography. After 9 hrs GC analysis showed 90.5% conversion of methyl amine and yield of methyl methyl carbamate was 60.43 mmol.

EXAMPLE—34

Methyl n-methyl carbamate was produced by charging following components to a 300 ml stirred autoclave:
Methyl amine: 193.5 mmol
Palladium metal: 4.72 mmol
Sodium iodide: 4.73 mmol
Methanol: 2222.75 mmol The reaction was carried out as per the procedure described in example 1, and liquid phase was analyzed by gas chromatography. After 7.5 hrs GC analysis showed 92.5% conversion of methyl amine and yield of methyl n-methyl carbamate was 120.21 mmol.

EXAMPLE—35

Methyl n-methyl carbamate was produced by charging following components to a 300 ml stirred autoclave:
Methyl amine: 242.35 mmol
Palladium metal: 4.72 mmol
Sodium iodide: 4.73 mmol
Methanol: 2150.79 mmol The reaction was carried out as per the procedure described in example 1, and liquid phase was analyzed by gas chromatography. After 8.5 hrs GC analysis showed 90.5% conversion of methyl amine and yield of methyl n-methyl carbamate was 103.08 mmol.

EXAMPLE—36

Methyl n-methyl carbamate was produced by charging following components to a 300 ml stirred autoclave:
N,N' Dimethyl urea: 224.70 mmol
Palladium metal: 4.72 mmol
Sodium iodide: 4.73 mmol
Methanol: 1975.79 mmol The reaction was carried out as per the procedure described in example 1, and liquid phase was analyzed by gas chromatography. After 9.0 hrs GC analysis showed 32.25% conversion of methyl amine and yield of methyl n-methyl carbamate was 121.51 mmol.

The inventive process is performed in a single step without the formation of toxic methyl isocyanate and is far less hazardous to perform than the conventional phosgenation process.

The process of the present invention operates under milder reaction conditions of temperature and pressure than hitherto known processes and a high selectivity to carbamates is achieved. The catalyst can be separated from the reaction crude simply by filtration and can be reused several times. Overall, therefore, the process of the present invention is expected to display considerable economical advantages over the known art.

We claim:

1. A process for the preparation of methyl methyl carbamate comprising reacting at least one compound selected from the group consisting of methyl amine and N,N'dimethyl urea with carbon monoxide, an oxidizing agent comprising oxygen and a monoalcohol in a reactor at suitable temperature and pressure conditions to optimize the formation of the methyl methyl carbamate, said temperature and pressure conditions comprising a carbon monoxide partial pressure of between about 100 and 1,500 psig, an oxygen partial pressure of between about 10 and 300 psig, and a temperature between about 140° and 350° C., said reaction being conducted in the presence of a catalyst system consisting essentially of (i) a precursor containing a platinum group metal, and (ii) at least one halogen containing promoter effective to promote said reaction, said at least one compound being charged to the reactor at a volume concentration of from about $3.2 \times 10^{-4}$ to about $1.6 \times 10^{-3}$ mol/cm$^3$, whereby to minimize a reverse reaction wherein the methyl, methyl carbamate reacts with $CH_3NH_2$ to form N,N'-dimethyl urea and $CH_3OH$ and thereby to optimize a yield of and selectivity for the methyl methyl carbamate, said monoalcohol and said carbon monoxide each being present in an amount of at least one mol per amine group of the methyl amine or per urea group of the N,N'-dimethyl urea, said oxidizing agent being present such that the oxygen is present in the reactor at a CO/O$_2$ ratio in the range of about 1:1 to 50:1 and said catalyst being employed in an amount of one mol of catalyst per 5 to 8000 mols of methylamine or dimethyl urea compound.

2. A process as claimed in claim 1, wherein the monoalcohol is an aliphatic monoalcolhol.

3. A process as claimed in claim 1, wherein O$_2$ is present in the reactor at a CO:O$_2$ ratio in the range of about 5:1 to 20:1.

4. A process as claimed in claim 3, wherein the ratio of halogen promotor to precursor is in the range of between about 0.1 and 10.

5. A process as claimed in claim 4, wherein the reaction is effected in the presence of a solvent.

6. A process as claimed in claim 5, wherein said solvent is selected from aromatic hydrocarbons such as benzene, toluene, xylene and mesitylene, nitriles such as acetonitrile and benzonitrile, ethers such as tetrahydrofuran and 2-dioxane, ketones such as acetone and methyl ethyl ketone, amides such as N,N'-dimethyl formamide and N,N'-dimethyl acetamide, and esters such as ethyl acetate and ethyl benzoate.

7. A process as claimed in claim 6, wherein the precursor of said catalyst system comprises palladium metal supported on a suitable carrier.

8. A process as claimed in claim 7, wherein the precursor is selected from the group consisting of Pd black, Pd-C, Pd-Al$_2$O, Pd-CaCO$_3$, Pd-Se, Pd-Co, Pd-Rh, PdCl$_2$, PdBr$_2$, PdI$_2$ Pd(NO$_3$)$_2$, Pd(OCOCH$_3$)$_2$, Pd-oxalate, [Pd(NH$_3$)$_4$] X$_2$, [PdL$_2$X], and [Pd(CO)X] wherein X is chlorine, bromine or iodine and L is triphenyl phosphine, pyridine, isoquinoline, tributyl phosphine, or benzonitrile.

9. A process as claimed in claim 8, wherein said halogen-containing promotor contains iodine.

10. A process as claimed in claim 9, wherein the halogen-containing promoter is selected from the group consisting of sodium iodide, potassium iodide, lithium iodide, cesium iodide, tetrabutyl ammonium iodide, tetraheptyl ammonium iodide, iodous acid, iodic acid, and iodine.

11. A process as claimed in claim 10, wherein said catalyst is employed in an amount of 1 mol of catalyst per 100 to 500 mols of methyl amine or dimethyl urea compound.

12. A process as claimed in claim 11, wherein the ratio of halogen promotor to precursor in the catalyst system is in the range of from about 0.5 to 5.

* * * * *